US012102407B2

(12) United States Patent
Kishida et al.

(10) Patent No.: US 12,102,407 B2
(45) Date of Patent: Oct. 1, 2024

(54) SURGICAL ROBOT

(71) Applicant: KAWASAKI JUKOGYO KABUSHIKI KAISHA, Kobe (JP)

(72) Inventors: Yuji Kishida, Kobe (JP); Tsuyoshi Tojo, Ibaraki (JP); Toshihiko Takagi, Kobe (JP); Hiroaki Kitatsuji, Kobe (JP); Koji Muneto, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 628 days.

(21) Appl. No.: 17/240,132

(22) Filed: Apr. 26, 2021

(65) Prior Publication Data

US 2021/0330410 A1    Oct. 28, 2021

(30) Foreign Application Priority Data

Apr. 28, 2020 (JP) ................. 2020-079001

(51) Int. Cl.
*A61B 34/00* (2016.01)
*A61B 34/30* (2016.01)
*A61B 34/37* (2016.01)

(52) U.S. Cl.
CPC .............. *A61B 34/74* (2016.02); *A61B 34/30* (2016.02); *A61B 2034/742* (2016.02)

(58) Field of Classification Search
CPC ... A61B 34/74; A61B 34/30; A61B 2034/742; A61B 2090/064; A61B 34/37; A61B 34/35
USPC ................. 700/245–264; 318/568.11–568.25
See application file for complete search history.

(56) References Cited

U.S. PATENT DOCUMENTS

| | | | |
|---|---|---|---|
| 6,331,181 B1 * | 12/2001 | Tierney ................. | G16H 40/63 606/130 |
| 7,574,250 B2 * | 8/2009 | Niemeyer .............. | A61B 90/36 600/407 |
| 7,955,322 B2 * | 6/2011 | Devengenzo .......... | B25J 9/1045 606/1 |
| 8,142,447 B2 * | 3/2012 | Cooper ................. | G16H 40/63 606/1 |
| 8,273,076 B2 | 9/2012 | Devengenzo et al. | |
| 8,827,948 B2 * | 9/2014 | Romo ..................... | A61B 6/12 604/95.04 |
| 8,961,533 B2 * | 2/2015 | Stahler .................. | A61B 34/35 606/108 |
| 9,795,453 B2 * | 10/2017 | Tierney ................. | A61B 34/35 |
| 10,265,869 B2 * | 4/2019 | Lohmeier .............. | A61B 90/40 |
| 11,173,597 B2 * | 11/2021 | Rabindran ............... | B25J 9/06 |
| 11,510,684 B2 * | 11/2022 | Blackwell .............. | A61B 34/20 |

(Continued)

FOREIGN PATENT DOCUMENTS

| | | |
|---|---|---|
| EP | 2879608 A0 | 2/2014 |
| JP | 2005-204999 A | 8/2005 |

(Continued)

*Primary Examiner* — Jaime Figueroa
(74) *Attorney, Agent, or Firm* — METROLEX IP LAW GROUP, PLLC; Robert L. Scott, Esq.

(57) ABSTRACT

In a surgical robot, an operation unit includes an enable switch and an operation tool configured to control a moving direction of an arm, and the enable switch and the operation tool are arranged apart from each other within a range operable by fingers of one hand of an operator in the operation unit.

19 Claims, 7 Drawing Sheets

(56) References Cited

U.S. PATENT DOCUMENTS

| | | | | |
|---|---|---|---|---|
| 2002/0032452 A1* | 3/2002 | Tierney | G06Q 30/02 | 606/130 |
| 2003/0114962 A1* | 6/2003 | Niemeyer | A61B 34/30 | 700/250 |
| 2005/0165271 A1 | 7/2005 | Shioda et al. | | |
| 2007/0012135 A1* | 1/2007 | Tierney | A61B 34/30 | 74/490.01 |
| 2009/0030428 A1* | 1/2009 | Omori | A61B 34/70 | 606/130 |
| 2009/0171374 A1* | 7/2009 | Omori | A61B 34/71 | 606/130 |
| 2009/0248043 A1* | 10/2009 | Tierney | A61B 46/13 | 606/130 |
| 2011/0040406 A1* | 2/2011 | Shioda | A61B 90/50 | 700/250 |
| 2012/0071895 A1* | 3/2012 | Stahler | A61B 34/35 | 606/130 |
| 2014/0094825 A1* | 4/2014 | Flaherty | B25J 13/06 | 606/130 |
| 2015/0012010 A1* | 1/2015 | Adler | A61B 34/37 | 606/130 |
| 2015/0066051 A1* | 3/2015 | Kwon | A61B 34/76 | 606/130 |
| 2015/0282828 A1* | 10/2015 | Kishi | A61B 34/30 | 606/205 |
| 2018/0101166 A1* | 4/2018 | Aldridge | B25J 9/1671 | |
| 2018/0116735 A1* | 5/2018 | Tierney | A61B 34/30 | |
| 2018/0243150 A1 | 8/2018 | Yano et al. | | |
| 2018/0271732 A1* | 9/2018 | Yano | A61G 13/04 | |
| 2018/0348744 A1* | 12/2018 | Cortsen | G05B 19/423 | |
| 2019/0143506 A1* | 5/2019 | Rabindran | B25J 3/04 | 700/253 |
| 2019/0143513 A1* | 5/2019 | Rabindran | B25J 9/1641 | 700/245 |
| 2019/0201137 A1* | 7/2019 | Shelton, IV | G16H 50/20 | |
| 2019/0365499 A1* | 12/2019 | Nagao | A61B 34/70 | |
| 2020/0121403 A1* | 4/2020 | Awano | B25J 9/1664 | |
| 2021/0007814 A1* | 1/2021 | Shuma | A61B 34/74 | |
| 2021/0128260 A1* | 5/2021 | Gonenc | A61B 34/32 | |

FOREIGN PATENT DOCUMENTS

| | | |
|---|---|---|
| JP | 2014-117783 A | 6/2014 |
| JP | 2015-020215 A | 2/2015 |
| JP | 2018-140166 A | 9/2018 |
| JP | 6562174 B1 | 8/2019 |
| JP | 2019-162427 A | 9/2019 |
| WO | 2014-022786 A2 | 2/2014 |
| WO | 2020/138032 A1 | 7/2020 |

* cited by examiner

SURGICAL ROBOT

CROSS-REFERENCE TO RELATED APPLICATION

The priority application number JP2020-079001, Surgical Robot, Apr. 28, 2020, Yuji Kishida, Tsuyoshi Tojo, Toshihiko Takagi, Hiroaki Kitatsuji, and Koji Muneto, upon which this patent application is based, is hereby incorporated by reference.

BACKGROUND OF THE INVENTION

Field of the Invention

The present disclosure relates to a surgical robot, and more particularly, it relates to a surgical robot including an operation tool to operate an arm.

Description of the Background Art

Conventionally, a surgical robot is known. Such a surgical robot is disclosed in Japanese Patent Laid-Open No. 2019-162427, for example.

Japanese Patent Laid-Open No. 2019-162427 discloses a robot system (surgical robot) including an articulated probe, a surgical instrument, and a controller (hereinafter referred to as an arm). The surgical instrument is provided at the tip end of the articulated probe. The arm is configured to operate (move) the articulated probe and the surgical instrument. The robot system further includes a joystick. When an operator operates the joystick, a signal for operating the surgical instrument is output to the arm. In addition, the displacement, speed, and acceleration of the surgical instrument are operated according to the displacement (a way to tilt) of the joystick. The joystick is arranged apart from the arm (the articulated probe and the surgical instrument).

However, in the robot system (surgical robot) as disclosed in Japanese Patent Laid-Open No. 2019-162427, at the time of surgery, the joystick arranged apart from the arm is operated such that the surgical instrument is operated. On the other hand, in the preparation stage before surgery, the arm is moved to move the surgical instrument to the vicinity of a patient. In this case, in the robot system as disclosed in Japanese Patent Laid-Open No. 2019-162427, the joystick is arranged apart from the arm, and thus it may be difficult to move the arm through the joystick so as to move the surgical instrument to the vicinity of the patient.

SUMMARY OF THE INVENTION

The present disclosure is intended to solve the above problem. The present disclosure aims to provide a surgical robot including an arm that can be easily operated.

In order to attain the aforementioned object, a surgical robot according to a first aspect of the present disclosure includes an arm, and an operation unit supported by the arm. The operation unit includes an enable switch configured to allow movement of the arm by being pressed, and an operation tool configured to control a moving direction of the arm, and the enable switch and the operation tool are arranged apart from each other within a range operable by fingers of one hand of an operator in the operation unit.

In the surgical robot according to the first aspect of the present disclosure, as described above, the operation unit is supported by the arm. Thus, the operator can operate the operation tool in the vicinity of the arm, and thus the arm can be easily operated through the operation tool.

When the operation unit is supported by the arm, movement of the operator may not be able to follow rapid movement of the arm when the arm moves at a relatively high speed (rapidly) due to the operation of the operation tool by the operator. Specifically, whereas the arm moves, the hand of the operator that grasps the operation tool cannot follow the movement of the arm and is stationary, or moves at a speed slower than the moving speed of the arm. In this case, the amount of operation on the operation tool changes against the intention of the operator, and the operating direction with respect to the arm changes against the intention of the operator. Consequently, the moving direction of the arm changes rapidly. On the contrary, even when the moving speed of the arm rapidly decreases, the operating direction with respect to the operation tool changes against the intention of the operator. When such a state continues, the arm operates so as to vibrate.

Therefore, as described above, the operation unit includes the enable switch that allows movement of the arm by being pressed and the operation tool that controls the moving direction of the arm, and the enable switch and the operation tool are arranged apart from each other within the range operable by the fingers of one hand of the operator in the operation unit. Accordingly, the operation tool configured to operate the moving direction of the arm can be operated by the finger of the operator while the operator presses the enable switch, and thus a distance between the finger of the operator that operates the operation tool and the finger of the operator that presses the enable switch is maintained substantially constant. That is, even when the arm moves at a relatively high speed, distances between the fingers of the operator that grasp the operation unit and the finger of the operator that operates the operation unit are maintained substantially constant. Thus, even when the arm moves at a relatively high speed, the state of the fingers of the operator with respect to the operation unit is unlikely to change, and thus the operating direction of the arm due to the operation unit is unlikely to change. Consequently, even when the arm moves at a relatively high speed, vibrations of the arm due to the change in the operating direction of the operation tool can be significantly reduced or prevented.

A surgical robot according to a second aspect of the present disclosure includes a robot arm including a plurality of joints, the robot arm being configured to allow a medical device to be attached to a tip end thereof, and an operation unit supported by the robot arm. The operation unit includes a joystick configured to operate the robot arm, and an enable switch configured to allow movement of the robot arm by being pressed, and the enable switch and the joystick are arranged apart from each other within a range operable by fingers of one hand of an operator in the operation unit.

In the surgical robot according to the second aspect of the present disclosure, as described above, the operation unit is supported by the arm. Thus, the operator can operate the operation tool in the vicinity of the arm, and thus the arm can be easily operated through the operation tool.

Furthermore, the enable switch and the joystick are arranged apart from each other within the range operable by the fingers of one hand of the operator in the operation unit such that even when the arm moves at a relatively high speed, vibrations of the arm due to a change in the operating direction of the operation tool can be significantly reduced or prevented, similarly to the surgical robot according to the first aspect.

A surgical robot according to a third aspect of the present disclosure includes a robot arm including an arm portion including a plurality of joints, and a translation mechanism provided on a tip end of the arm portion, the translation mechanism being configured to allow a medical device to be attached thereto, the translation mechanism being configured to translate the medical device relative to the arm portion, and an operation unit supported by the robot arm. The operation unit includes a switch unit configured to operate the translation mechanism, and an enable switch configured to allow movement of the robot arm by being pressed, and the enable switch and the switch unit are arranged apart from each other within a range operable by fingers of one hand of an operator in the operation unit.

In the surgical robot according to the third aspect of the present disclosure, as described above, the operation unit is supported by the arm. Thus, the operator can operate the operation tool in the vicinity of the arm, and thus the arm can be easily operated through the operation tool.

Furthermore, the enable switch and the switch unit are arranged apart from each other within the range operable by the fingers of one hand of the operator in the operation unit such that even when the arm moves at a relatively high speed, vibrations of the arm due to a change in the operating direction of the operation tool can be significantly reduced or prevented, similarly to the surgical robot according to the first aspect.

According to the present disclosure, as described above, the arm can be easily operated.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
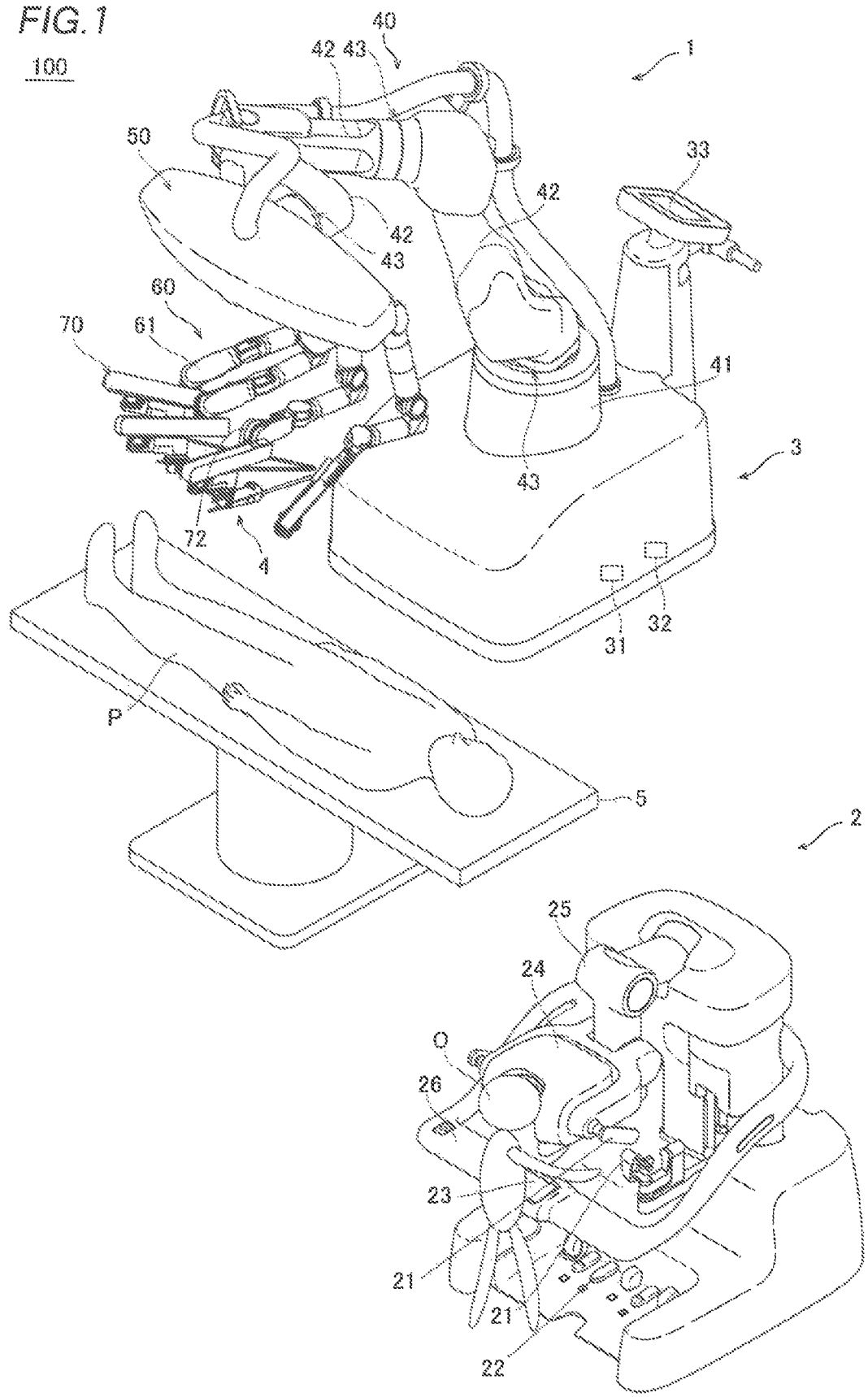
FIG. 1 is a diagram showing the configuration of a surgical system according to an embodiment of the present disclosure.

An embodiment of the present disclosure is hereinafter described with reference to the drawings.

The configuration of a surgical system 100 according to this embodiment is now described with reference to FIGS. 1 to 10. The surgical system 100 includes a medical manipulator 1 that is a patient P-side device and a remote operation device 2 that is an operator-side device configured to operate the medical manipulator 1. The medical manipulator 1 includes a medical cart 3, and is configured to be movable. The remote operation device 2 is arranged apart from the medical manipulator 1, and the medical manipulator 1 is configured to be remotely operated by the remote operation device 2. A surgeon inputs a command to the remote operation device 2 to cause the medical manipulator 1 to perform a desired operation. The remote operation device 2 transmits the input command to the medical manipulator 1. The medical manipulator 1 operates based on the received command. The medical manipulator 1 is arranged in an operating room that is a sterilized sterile field. The medical manipulator 1 is an example of a "surgical robot" in the claims.

The remote operation device 2 is arranged inside or outside the operating room, for example. The remote operation device 2 includes operation manipulator arms 21, operation pedals 22, a touch panel 23, a monitor 24, a support arm 25, and a support bar 26. The operation manipulator arms 21 define operation handles for the surgeon to input commands. The monitor 24 is a scope-type display that displays an image captured by an endoscope. The support arm 25 supports the monitor 24 so as to align the height of the monitor 24 with the height of the surgeon's face. The touch panel 23 is arranged on the support bar 26. The surgeon's head is detected by a sensor (not shown) provided in the vicinity of the monitor 24 such that the medical manipulator 1 can be operated by the remote operation device 2. The surgeon operates the operation manipulator arms 21 and the operation pedals 22 while visually recognizing an affected area on the monitor 24. Thus, a command is input to the remote operation device 2. The command input to the remote operation device 2 is transmitted to the medical manipulator 1.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote operation device 2.

The medical cart 3 includes an input 33. The input 33 is configured to receive operations to move a positioner 40, an arm base 50, and a plurality of arms 60 or change their postures mainly in order to prepare for surgery before the surgery. The arms 60 are examples of a "robot arm" in the claims.

Figure 2:
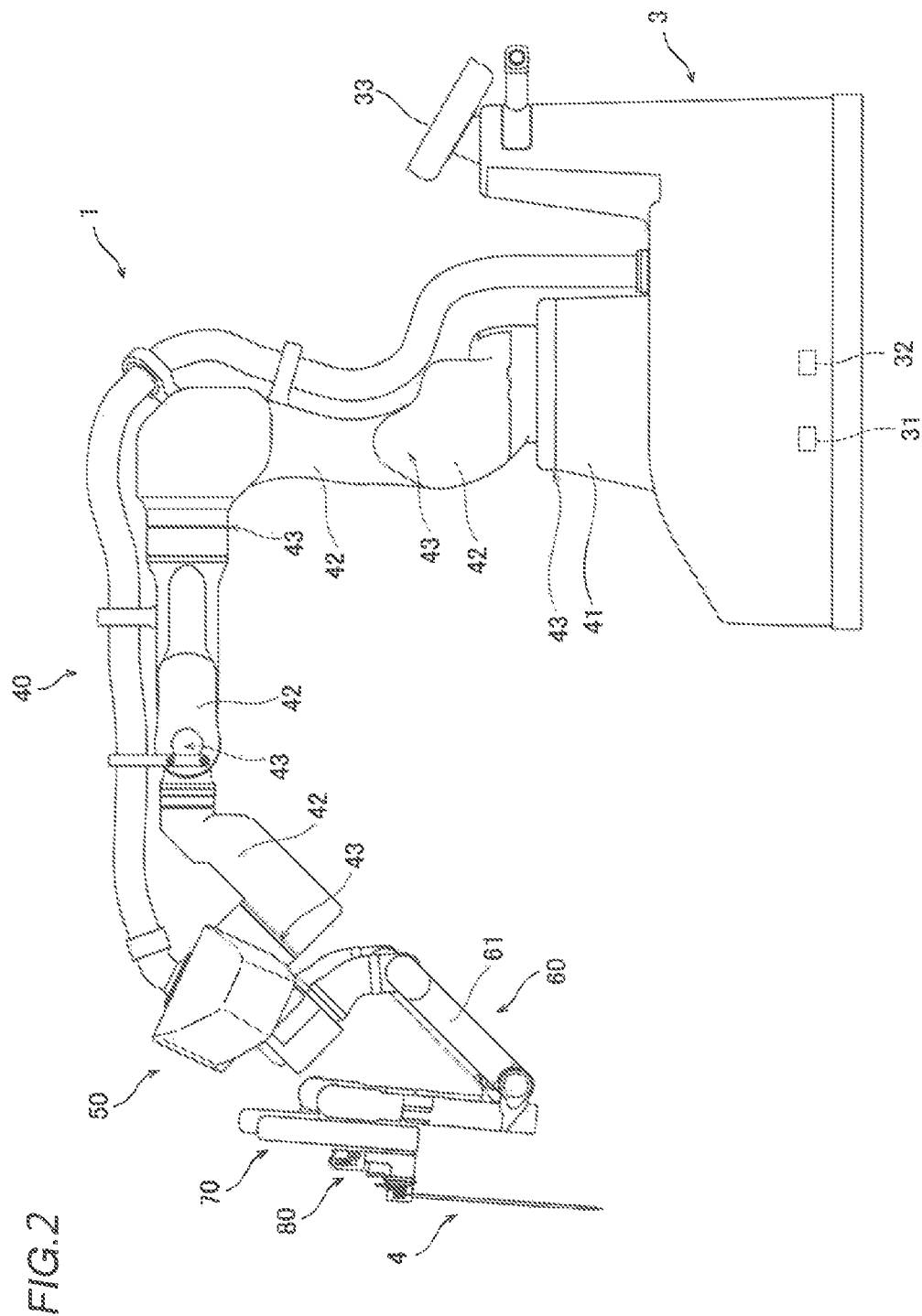
FIG. 2 is a diagram showing the configuration of a medical manipulator according to the embodiment of the present disclosure.

As shown in FIGS. 1 and 2, the medical manipulator 1 is arranged in the operating room. The medical manipulator 1 includes the medical cart 3, the positioner 40, the arm base 50, and the plurality of arms 60. The arm base 50 is attached to the tip end of the positioner 40. The arm base 50 has a relatively long rod shape (long shape). The bases of the plurality of arms 60 are attached to the arm base 50. Each of the plurality of arms 60 is configured to be able to take a folded posture (stored posture). The arm base 50 and the plurality of arms 60 are covered with sterile drapes (not shown) and used.

The positioner 40 includes a 7-axis articulated robot, for example. The positioner 40 is arranged on the medical cart 3. The positioner 40 is configured to move the position of the arm base 50 three-dimensionally.

The positioner 40 includes a base 41 and a plurality of links 42 coupled to the base 41. The plurality of links 42 are coupled to each other by joints 43.

As shown in FIG. 1, a medical device 4 is attached to the tip end of each of the plurality of arms 60. The medical device 4 includes a replaceable instrument or an endoscope assembly (not shown), for example.

Figure 3:
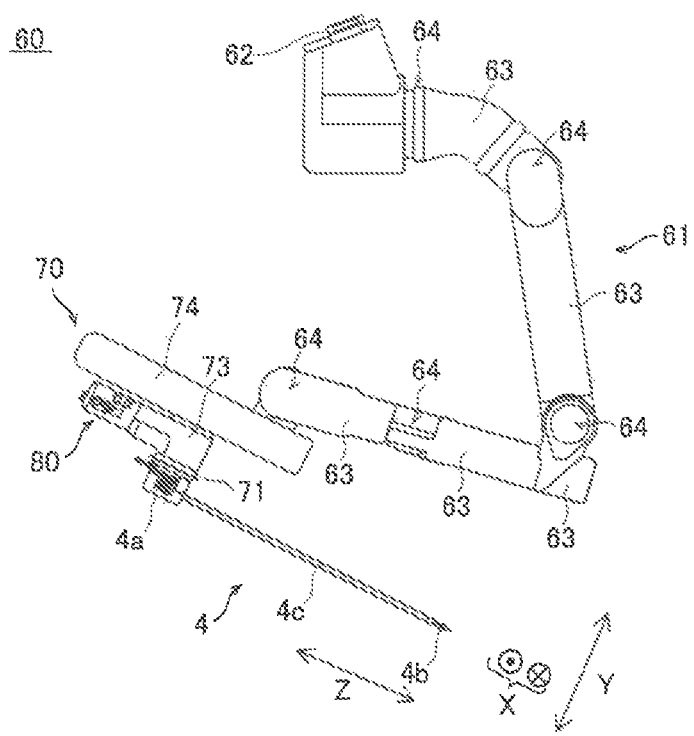
FIG. 3 is a diagram showing the configuration of an arm of the medical manipulator according to the embodiment of the present disclosure.

As shown in FIG. 3, the instrument as the medical device 4 includes a driven unit 4a driven by a servomotor M2 provided in a holder 71 of each of the arms 60. An end effector 4b is provided at the tip end of the instrument. The end effector 4b includes a pair of forceps, a pair of scissors, a grasper, a needle holder, a microdissector, a stable applier, a tacker, a suction cleaning tool, a snare wire, a clip applier, etc. as instruments having joints. The end effector 4b includes a cutting blade, a cautery probe, a washer, a catheter, a suction orifice, etc. as instruments having no joint. The medical device 4 includes a shaft 4c that connects the driven unit 4a to the end effector 4b. The driven unit 4a, the shaft 4c, and the end effector 4b are arranged along a Z direction.

The configuration of the arms 60 is now described in detail.

As shown in FIG. 3, each of the arms 60 includes an arm portion 61 (a base 62, links 63, and joints 64) and a translation mechanism 70 provided at the tip end of the arm portion 61. The arms 60 are configured to three-dimensionally move the tip end sides with respect to the base sides (arm base 50) of the arms 60. The plurality of arms 60 have the same configuration as each other.

In this embodiment, the medical device 4 is attached to the translation mechanism 70, and the translation mechanism 70 is configured to translate the medical device 4 relative to the arm portion 61. Specifically, the translation mechanism 70 includes the holder 71 configured to hold the medical device 4. The servomotor M2 (see FIG. 9) is housed in the holder 71. The servomotor M2 is configured to rotate a rotating body provided in the driven unit 4a of the medical device 4. The rotating body of the driven unit 4a is rotated such that the end effector 4b is operated.

The arms 60 are configured to be removable from the arm base 50.

The arm portion 61 includes a 7-axis articulated robot arm. The arm portion 61 includes the base 62 configured to attach the arm portion 61 to the arm base 50, and a plurality of links 63 coupled to the base 62. The plurality of links 63 are coupled to each other by the joints 64.

The translation mechanism 70 is configured to translate the medical device 4 attached to the holder 71 along the Z direction (a direction in which the shaft 4c extends) by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the medical device 4 provided on the holder 71 is translated along the Z direction. The tip end of the arm portion 61 is connected to the base end side link 72 so as to rotate the base end side link 72 about a Y direction orthogonal to the Z direction.

Figure 4:
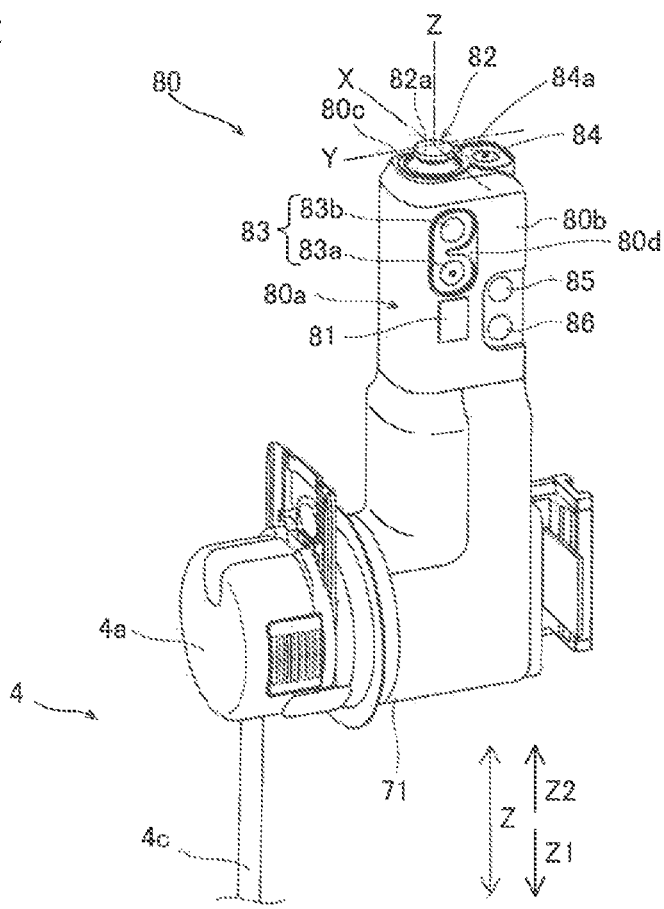
FIG. 4 is a perspective view showing the configuration of an operation unit of the medical manipulator according to the embodiment of the present disclosure.

In this embodiment, as shown in FIG. 4, the medical manipulator 1 includes an operation unit 80 supported by each of the arms 60. The operation unit 80 includes enable switches 81, a joystick 82 configured to operate movement of the medical device 4 by the arm 60, and switch units 83 configured to operate movement of the medical device 4 by the arm 60. The enable switches 81 allow movement of the arm 60 through the joystick 82 and the switch units 83, and get into a state of allowing movement of the arm 60 when the enable switches 81 are pressed. The joystick 82 controls (operates) the moving direction and moving speed of the arm 60. The enable switches 81 and the joystick 82 are arranged apart from each other within a range operable by the fingers of one hand of an operator O (such as a nurse or a technician) in the operation unit 80. The operation unit 80 is grasped and operated by the operator O. The operation unit 80 is configured to be operable by the finger of the operator O while the operator O grasps the operation unit 80 and presses the enable switches 81 to allow movement of the arm 60. The joystick 82 and the switch units 83 are examples of "operation tool" in the claims.

Specifically, the enable switches 81 are push-button switches pressed by the fingers of the operator O. The enable switches 81 are pressed such that it becomes possible to perform a control to energize servomotors M1 to M3 (see FIG. 9) (perform a control to drive the servomotors M1 to M3). That is, it becomes possible to perform a control to move the arm 60 only while the enable switches 81 are pressed.

The operator O tilts the joystick 82 with their finger such that the joystick 82 is operated. The arm 60 is controlled to be moved according to a direction in which the joystick 82 is tilted and an angle at which the joystick 82 is tilted. The operator O brings their finger into contact with the tip end 82a of the joystick 82, moves their finger, and tilts the joystick 82 to operate the joystick 82. Only while the enable switches 81 are pressed, a signal input based on the operation of the joystick 82 is received. That is, when the enable switches 81 are not pressed, the arm 60 is not moved even when the joystick 82 is operated.

Figure 5:
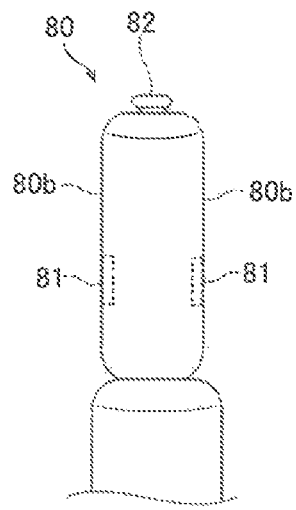
FIG. 5 is a side view showing the configuration of the operation unit of the medical manipulator according to the embodiment of the present disclosure.

In this embodiment, the enable switches 81 are provided on the outer peripheral surface 80a of the operation unit 80, and allow movement of the arm 60 when the operator O grasps the outer peripheral surface 80a of the operation unit 80 and presses the enable switches 81. As shown in FIG. 5, a pair of enable switches 81 are provided on opposite sides of the outer peripheral surface 80a of the operation unit 80. Specifically, the cross-section of the operation unit 80 has a substantially rectangular shape, and the pair of enable switches 81 are provided on surfaces 80b of the operation unit 80 that face each other, respectively. More specifically, the operation unit 80 has a substantially prismatic shape, and the pair of enable switches 81 are provided on the side surfaces (the surfaces 80b along a longitudinal direction) of the substantially prismatic operation unit 80. The operator O grasps the outer peripheral surface 80a of the operation unit 80 and presses at least one of the enable switches 81 provided on the opposite sides of the outer peripheral surface 80a of the operation unit 80 to allow movement of the arm 60.

Thus, it is not necessary to press both of the enable switches 81 provided on the opposite sides of the outer peripheral surface 80a of the operation unit 80, and thus the burden on the operator O can be reduced while the convenience of the operator O is improved.

Figure 6:
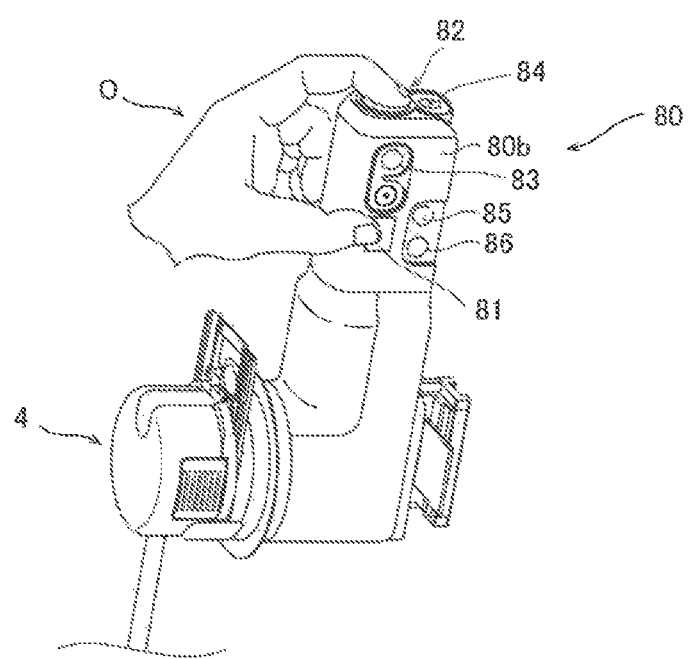
FIG. 6 is a diagram showing a state in which an operator grasps the operation unit of the medical manipulator according to the embodiment of the present disclosure.

In this embodiment, as shown in FIG. 5, the joystick 82 is provided on an end face 80c of the operation unit 80 that intersects with the outer peripheral surface 80a. The joystick 82 is arranged at a position operable by the finger of the operator O while the operator O grasps the outer peripheral surface 80a of the operation unit 80 and presses the enable switches 81 to allow movement of the arm 60. For example, as shown in FIG. 6, the operator O operates the joystick 82 provided on the end face 80c of the operation unit 80 with their index finger or the like while pressing the pair of enable switches 81 provided on the outer peripheral surface 80a of the operation unit 80 with their thumb and middle finger or the like. Thus, substantially constant distances between the thumb and middle finger of the operator O that grasp the operation unit 80 and the index finger of the operator O that operates the joystick 82 can be easily maintained. Which fingers are used to operate the enable switches 81 and the joystick 82 is not limited to the above example.

In this embodiment, the joystick 82 is configured to operate movement of the medical device 4 by the arm 60 such that the tip end 4d (see FIG. 7 or FIG. 8) of the medical device 4 moves on a predetermined plane or the medical device 4 rotates about the tip end 4d of the medical device 4. The operation unit 80 includes the switch units 83 configured to operate movement of the medical device 4 by the arm 60 such that the tip end 4d of the medical device 4 moves along the longitudinal direction of the medical device 4. The predetermined plane on which the tip end 4d of the medical device 4 moves refers to a plane (an X-Y plane in FIG. 4) parallel to the end face 80c of the operation unit 80. The longitudinal direction of the medical device 4 refers to the Z direction orthogonal to the X-Y plane in FIG. 4. Coordinates represented by an X-axis, a Y-axis, and a Z-axis in FIG. 4 are referred to as a tool coordinate system (or a base coordinate system). When the switch units 83 are pressed while the enable switches 81 are pressed (while movement of the medical device 4 by the arm 60 is allowed), the tip end 4d of the medical device 4 is moved along the longitudinal direction of the medical device 4.

A pair of switch units 83 are provided on the opposite sides of the outer peripheral surface 80a of the operation portion 80. The operator O grasps the outer peripheral surface 80a of the operation unit 80 and presses at least one of the switch units 83 provided on the opposite sides of the outer peripheral surface 80a of the operation unit 80 to cause the translation mechanism 70 to move the medical device 4.

In this embodiment, the moving speed of the tip end 4d of the medical device 4 is changed according to the tilted state of the joystick 82, and when the joystick 82 is maximally tilted, the moving speed of the tip end 4d of the medical device 4 on the predetermined plane is maximized. The time until the switch units 83 are pressed by the operator O and the moving speed of the tip end 4d of the medical device 4 along the longitudinal direction of the medical device 4 orthogonal to the predetermined plane is maximized is longer than the time until the joystick 82 is operated by the operator O and the moving speed of the tip end 4d of the medical device 4 is maximized. That is, the joystick 82 is operated such that the tip end 4d of the medical device 4 is moved at a relatively high speed. On the other hand, the switch units 83 are operated such that the tip end 4d of the medical device 4 is moved at a relatively low speed.

In this embodiment, each of the switch units 83 includes a switch 83a configured to move the tip end 4d of the medical device 4 in a direction in which the medical device 4 is inserted into the patient P, parallel to the longitudinal direction of the medical device 4, and a switch 83b configured to move the tip end 4d of the medical device 4 in a direction opposite to the direction in which the medical device 4 is inserted into the patient P. Both the switch 83a and the switch 83b are push-button switches. Each of the switches 83a and 83b has a substantially circular shape. The direction in which the medical device 4 is inserted into the patient P is an example of a "first direction" in the claims. The direction opposite to the direction in which the medical device 4 is inserted into the patient P is an example of a "second direction" in the claims. The switch 83a and the switch 83b are examples of a "first switch" and a "second switch" in the claims, respectively.

Pivot buttons 85 are provided adjacent to the enable switches 81 on the surfaces 80b of the operation unit 80. The pivot buttons 85 are configured to set a pivot point. The pivot point refers to a fulcrum on which the arm 60 operates. Adjustment buttons 86 for optimizing the position of the arm 60 are provided on the surfaces 80b of the operation unit 80.

In this embodiment, when the switch units 83 are operated before a pivot position PP is set, the arm portion 61 is moved such that the tip end 4d of the medical device 4 is translated. When the switch units 83 are operated after the pivot position PP is set, the arm portion 61 is moved such that the tip end 4d of the medical device 4 is translated until the tip end 4d of the medical device 4 is moved by a predetermined distance from the pivot position PP. After the tip end 4d of the medical device 4 is moved by the predetermined distance from the pivot position PP, the translation mechanism 70 is moved such that the tip end 4d of the medical device 4 is translated. That is, after the tip end 4d of the medical device 4 is moved by the predetermined distance from the pivot position PP, the arm portion 61 is not moved but only the translation mechanism 70 is moved.

Figure 7:
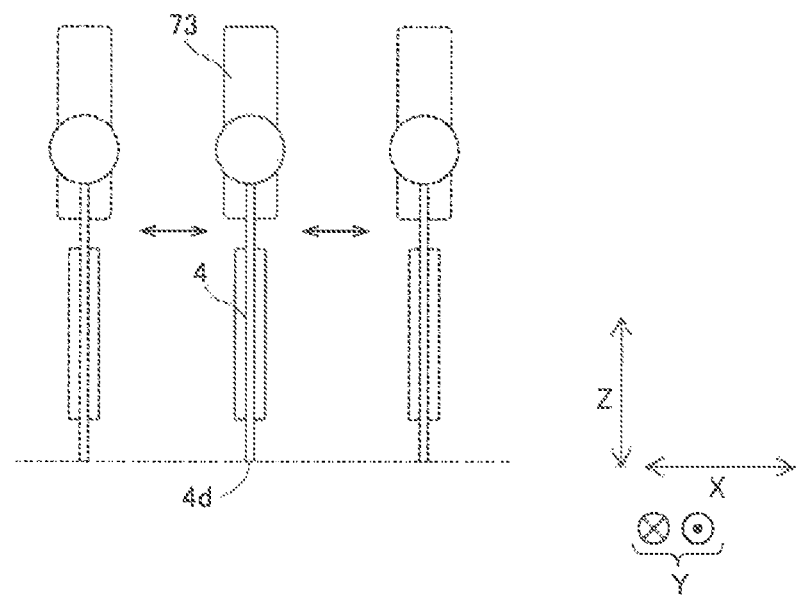
FIG. 7 is a diagram for illustrating translation of the arm.
Figure 8:
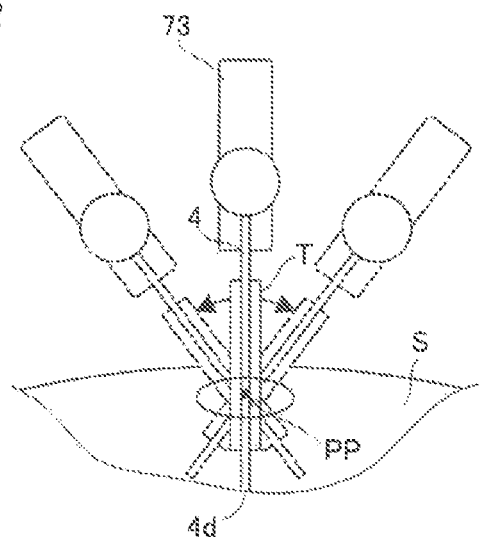
FIG. 8 is a diagram for illustrating rotation of the arm.

In this embodiment, as shown in FIG. 4, the operation unit 80 includes a mode switching button 84 configured to switch between a mode for translating the tip end 4d of the medical device 4 attached to the arm 60 in the predetermined plane (see FIG. 7) and a mode for rotating the medical device 4 about the tip end 4d of the medical device 4 (see FIG. 8). In the operation unit 80, the mode switching button 84 is arranged in the vicinity of the joystick 82. Specifically, on the end face 80c of the operation unit 80, the mode switching button 84 is provided adjacent to the joystick 82. The mode switching button 84 is a push-button switch. Furthermore, a mode indicator 84a is provided in the vicinity of the mode switching button 84. The mode indicator 84a is turned on or off such that a current mode (translation mode or rotation mode) is indicated.

As shown in FIG. 7, in the translation mode for translating the tip end 4d of the medical device 4, the arm 60 is moved through the joystick 82 such that the tip end 4d of the medical device 4 moves on the X-Y plane. As shown in FIG. 8, in the rotation mode for rotating the tip end 4d of the medical device 4, when the pivot position PP is not taught, the arm 60 is moved through the joystick 82 such that the medical device 4 rotates about the tip end 4d of the end effector 4b, and when the pivot position PP is taught, the arm 60 is moved through the joystick 82 such that the medical device 4 rotates about the pivot position PP as a fulcrum. After the pivot point (pivot position PP) is set, the translation mode cannot be set. When the shaft 4c of the medical device 4 is inserted into a trocar T, the medical device 4 is rotated while the shaft 4c is restrained with the pivot position PP as a fulcrum.

That is, the joystick 82 is configured to operate the arm in one of the translation mode in which the arm 60 moves the medical device 4 such that the tip end 4d of the medical device 4 attached to the arm 60 translates in the predetermined plane (see FIG. 7) and the rotation mode in which the arm 60 moves the medical device 4 such that the medical device 4 rotates about the tip end 4d of the medical device 4 (see FIG. 8).

In this embodiment, as shown in FIG. 3, the operation unit 80 is provided on the translation mechanism 70. The operation unit 80 is supported by the translation mechanism 70 so as to be adjacent to the medical device 4 attached to the translation mechanism 70. Specifically, the operation unit 80 is attached to the tip end side link 73 of the translation mechanism 70. The operation unit 80 is arranged adjacent to the driven unit 4a of the medical device 4.

Figure 9:
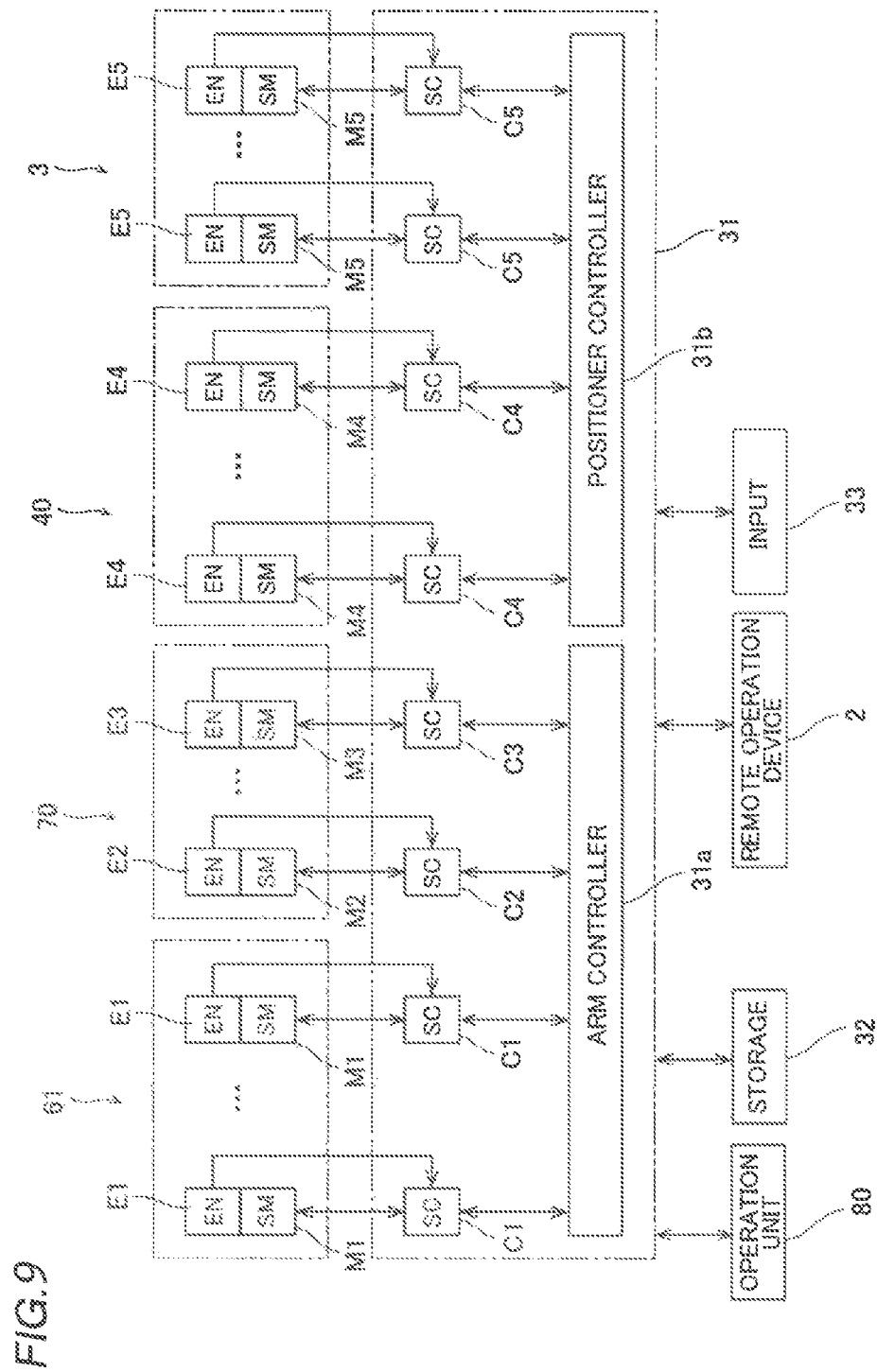
FIG. 9 is a block diagram showing the configuration of a controller of the medical manipulator according to the embodiment of the present disclosure.

As shown in FIG. 9, the arm 60 includes a plurality of servomotors M1, encoders E1, and speed reducers (not shown) so as to correspond to a plurality of joints 64 of the arm portion 61. The encoders E1 are configured to detect the rotation angles of the servomotors M1. The speed reducers are configured to slow down rotation of the servomotors M1 to increase the torques.

As shown in FIG. 9, the translation mechanism 70 includes the servomotor M2 configured to rotate the rotating body provided in the driven unit 4a of the medical device 4, the servomotor M3 configured to translate the medical device 4, encoders E2 and E3, and speed reducers (not shown). The encoders E2 and E3 are configured to detect the rotation angles of the servomotors M2 and M3, respectively. The speed reducers are configured to slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 are configured to detect the rotation angles of the servomotors M4. The speed reducers are configured to slow down rotation of the servomotors M4 to increase the torques.

The medical cart 3 includes servomotors M5 configured to drive a plurality of front wheels (not shown) of the medical cart 3, respectively, encoders E5, and speed reducers (not shown). The encoders E5 are configured to detect the rotation angles of the servomotors M5. The speed reducers are configured to slow down rotation of the servomotors M5 to increase the torques.

The controller 31 of the medical cart 3 includes an arm controller 31a that controls movement of the plurality of arms 60 based on commands, and a positioner controller 31b that controls movement of the positioner 40 and driving of the front wheels (not shown) of the medical cart 3 based on commands. Servo controllers C1 configured to control the servomotors M1 configured to drive the arm 60 are electrically connected to the arm controller 31a. The encoders E1 configured to detect the rotation angles of the servomotors M1 are electrically connected to the servo controllers C1.

A servo controller C2 configured to control the servomotor M2 configured to drive the medical device 4 is electrically connected to the arm controller 31a. The encoder E2 configured to detect the rotation angle of the servomotor M2 is electrically connected to the servo controller C2. A servo controller C3 configured to control the servomotor M3 configured to translate the translation mechanism 70 is electrically connected to the arm controller 31a. The encoder E3 configured to detect the rotation angle of the servomotor M3 is electrically connected to the servo controller C3.

An operation command input to the remote operation device 2 is input to the arm controller 31a. The arm controller 31a generates position commands based on the input operation command and the rotation angles detected by the encoders E1 (E2 or E3), and outputs the position commands to the servo controllers C1 (C2 or C3). The servo controllers C1 (C2 or C3) generate torque commands based on the position commands input from the arm controller 31a and the rotation angles detected by the encoders E1 (E2 or E3), and output the torque commands to the servomotors M1 (M2 or M3). Thus, the arm 60 is moved according to the operation command input to the remote operation device 2.

In this embodiment, the controller 31 (arm controller 31a) is configured to operate the arm 60 based on an input signal from the joystick 82 of the operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31a and the rotation angles detected by the encoders E1, and output the torque commands to the servomotors M1. Thus, the arm 60 is moved according to the operation command input to the joystick 82.

In this embodiment, the controller 31 (arm controller 31a) is configured to perform a control to reduce a change in the moving speed of the arm 60 by performing at least one of setting an upper limit for the input signal from the joystick 82 or smoothing the input signal from the joystick 82. Specifically, the controller 31 controls movement of the arm 60 using the upper limit as the input signal when the upper limit is set for the input signal from the joystick 82, and an input signal exceeding the upper limit is input. Furthermore, the controller 31 smooths the input signal from the joystick 82 by a low-pass filter (LPF), for example. In this embodiment, the controller 31 performs both of setting the upper limit for the input signal from the joystick 82 and smoothing the input signal from the joystick 82.

The controller 31 (arm controller 31a) controls movement of the arm 60 based on an equation of motion for control shown in the following mathematical formula.

$$m\ddot{x} = c\dot{x} = F + \beta \dot{F}$$

Figure 10:
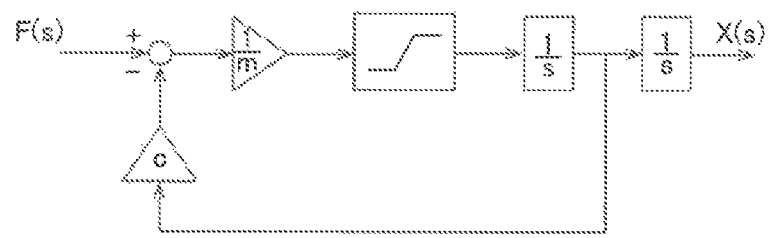
FIG. 10 is a diagram showing control blocks of the controller of the medical manipulator according to the embodiment of the present disclosure.

The controller 31 (arm controller 31a) controls movement of the arm 60 based on control blocks shown in FIG. 10. That is, the controller 31 (arm controller 31a) subtracts the product of the speed (a first order differential of x) and the viscosity coefficient c from the input signal F(s) from the joystick 82. Then, the subtracted value is multiplied by an inertia coefficient 1/m. When the multiplied value (=1/m(F(s)−c×speed)=acceleration=second order differential of x) exceeds the upper limit, the acceleration is set to the upper limit. Then, the acceleration is integrated to calculate the speed (the first order differential of x), and the speed is integrated to calculate a position X(s).

Servo controllers C4 configured to control the servomotors M4 that move the positioner 40 are electrically connected to the positioner controller 31b. The encoders E4 configured to detect the rotation angles of the servomotors M4 are electrically connected to the servo controllers C4. Servo controllers C5 configured to control the servomotors M5 that drive the front wheels (not shown) of the medical cart 3 are electrically connected to the positioner controller 31b. The encoders E5 configured to detect the rotation angles of the servomotors M5 are electrically connected to the servo controllers C5.

An operation command regarding preparation position setting, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate torque commands based on the position commands input from the positioner controller 31b and the rotation angles detected by the encoders E4, and output the torque commands to the servomotors M4. Thus, the positioner 40 is moved according to the operation command input to the input 33. Similarly, the positioner controller 31b moves the medical cart 3 based on an operation command from the input 33.

The procedure of surgery using the medical manipulator 1 is now described. In the surgery using the medical manipulator 1, the medical cart 3 is first moved to a predetermined position in the operating room by the operator O. Next, the operator O operates a touch panel of the input 33 to operate the positioner 40 such that the arm base 50 and a surgical table 5 or the patient P have a desired positional relationship, and moves the base 50. Furthermore, the arm 60 is moved such that a cannula sleeve (a working channel for inserting a surgical instrument or the like into the body cavity) arranged on the body surface of the patient P and the medical device 4 have a predetermined positional relationship. The joysticks 82 is operated by the operator O such that the plurality of arms 60 are moved to desired positions. Then, with the positioner 40 being stationary, the plurality of arms 60 and the medical devices 4 are operated based on commands from the remote operation device 2. Thus, the surgery with the medical manipulator 1 is performed.

Advantages of this Embodiment

According to this embodiment, the following advantages are achieved.

According to this embodiment, as described above, the operation unit 80 is supported by the arm 60. Accordingly, the operator O can operate the joystick 82 and the switch units 83 in the vicinity of the arm 60, and thus the arm 60 can be easily operated through the operation tool.

According to this embodiment, as described above, the operation unit 80 includes the enable switches 81 configured to allow movement of the arm 60 by being pressed and the joystick 82 configured to control (operate) the moving direction and moving speed of the arm 60, and the enable switches 81 and the joystick 82 are arranged apart from each other within the range operable by the fingers of one hand of the operator O in the operation unit 80. Accordingly, the joystick 82 configured to operate the moving direction and moving speed of the arm 60 can be operated by the finger of the operator O while the operator O presses the enable switches 81, and thus the distances between the finger of the operator O that operates the joystick 82 and the fingers of the operator O that press the enable switches 81 are maintained substantially constant. That is, even when the arm 60 moves at a relatively high speed, the distances between the fingers of the operator O that grasp the operation unit 80 and the finger of the operator O that operates the operation unit 80 are maintained substantially constant. Thus, even when the arm 60 moves at a relatively high speed, the state of the fingers of the operator O with respect to the operation unit 80 is unlikely to change, and thus the direction of the arm 60 due to the operation unit 80 is unlikely to change. Consequently, even when the arm 60 moves at a relatively high speed, vibrations of the arm 60 due to the change in the direction of the joystick 82 can be significantly reduced or prevented.

According to this embodiment, as described above, the joystick 82 is configured to operate the moving direction and moving speed of the arm 60. Accordingly, vibrations of the arm 60 due to a change in the direction of the joystick 82 and a change in the amount of operation can be significantly reduced or prevented.

According to this embodiment, as described above, the enable switches 81 are provided on the outer peripheral surface 80a of the operation unit 80, and the operator O grasps the outer peripheral surface 80a of the operation unit 80 and presses the enable switches 81 to allow movement of the arm 60. Accordingly, the operator O can easily press the enable switches 81 to allow movement of the arm 60 simply by grasping the outer peripheral surface 80a of the operation unit 80 so as to cover the same with their fingers.

According to this embodiment, as described above, the pair of enable switches 81 are provided on the opposite sides of the outer peripheral surface 80a of the operation unit 80, and the operator O grasps the outer peripheral surface 80a of the operation unit 80 and presses at least one of the enable switches 81 to allow movement of the arm 60. Accordingly, the enable switches 81 are provided on the opposite sides of the outer peripheral surface 80a of the operation unit 80, and thus the operator O can be encouraged to cover and grasp the outer peripheral surface 80a of the operation unit 80 with their fingers. Furthermore, the arm is configured to be allowed to move by pressing only one of the enable switches 81 such that the operator O can perform an operation to move the arm 60 by pressing the enable switch 81 that is easier to press, and thus the convenience of the operation can be improved.

According to this embodiment, as described above, the cross-section of the operation unit 80 has a substantially rectangular shape, and the pair of enable switches 81 are provided on the surfaces 80b of the operation unit 80 that face each other, respectively. Accordingly, the pair of enable switches 81 are provided on the surfaces 80b of the operation unit 80 that face each other, respectively, and thus the operator O can easily press the enable switches 81 by grasping the operation unit 80 so as to sandwich the surfaces 80b that face each other.

According to this embodiment, as described above, the joystick 82 is arranged at the position operable by the finger of the operator O while the operator O grasps the outer peripheral surface 80a of the operation unit 80 and presses the enable switches 81. Accordingly, the operator O can operate, with their index finger or the like, the joystick 82 provided on the end face 80c that intersects with the outer peripheral surface 80a of the operation unit 80 while pressing, with their thumb and middle finger or the like, the enable switches 81 provided on the outer peripheral surface 80a of the operation unit 80, for example. Thus, the distances between the thumb and middle finger or the like of the operator O that grasp the operation unit 80 and the index finger of the operator O that operates the operation unit 80 can be easily maintained substantially constant.

According to this embodiment, as described above, the arm 60 includes the arm portion 61 including a 7-axis articulated robot arm and the translation mechanism 70 provided at the tip end of the arm portion 61, configured to allow the medical device 4 to be attached thereto, and configured to translate the medical device 4 relative to the arm portion 61. Accordingly, the operation unit 80 is arranged in the vicinity (the translation mechanism 70 to which the medical device 4 is attached) of the medical device 4, and thus an operation to move the arm 60 so as to move the medical device 4 to a desired position can be easily performed by the operation unit 80.

According to this embodiment, as described above, the operation unit 80 is supported by the translation mechanism 70 so as to be adjacent to the medical device 4. Accordingly, the operation unit 80 is reliably arranged in the vicinity of the medical device 4, and thus an operation to move the arm 60 so as to move the medical device 4 to a desired position can be more easily performed by the operation unit 80.

According to this embodiment, as described above, the operation unit 80 includes the joystick 82 configured to be operable by the finger of the operator O. Accordingly, the joystick 82 can be operated with a relatively small force, and thus the operator O can easily operate the joystick 82 with their finger while grasping the outer peripheral surface 80a of the operation unit 80 and pressing the enable switches 81 to allow movement of the arm 60.

According to this embodiment, the operation unit 80 further includes the switch units 83 configured to operate the arm 60 such that the tip end 4d of the medical device 4 moves along the longitudinal direction of the medical device 4. Accordingly, the joystick 82 and the switch units 83 are used together such that the arm 60 can be moved three-dimensionally.

According to this embodiment, as described above, the joystick 82 operates the moving direction and moving speed of the arm 60, and the medical manipulator 1 includes the controller 31 that controls the arm 60 based on the input signal from the joystick 82. Furthermore, the controller 31 is configured to perform a control to reduce a change in the moving speed of the arm 60 by performing at least one of setting the upper limit for the input signal from the joystick 82 or smoothing the input signal from the joystick 82. Accordingly, even when the arm 60 moves at a higher speed and the amount of operation of the finger of the operator O on the operation unit 80 changes, at least one of setting the upper limit for the input signal from the joystick 82 or smoothing the input signal from the joystick 82 is performed by the controller 31 such that vibrations of the arm 60 due to the change in the amount of operation of the joystick 82 can be more effectively significantly reduced or prevented.

Modified Examples

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the operation unit 80 includes the joystick 82 configured to be operable by the finger of the operator O in the aforementioned embodiment, the present disclosure is not limited to this. For example, the operation unit 80 may alternatively include an acceleration sensor configured to be operable by the finger of the operator O, and the arm 60 may alternatively be moved based on an input signal to the acceleration sensor. Alternatively, the operation unit 80 may include a force sensor configured to be operable by the finger of the operator O, and the arm 60 may be moved based on an input signal to the force sensor. As the force sensor, a strain gauge force sensor or a piezoelectric force sensor is used, for example. Furthermore, as the force sensor, a 3-axis force sensor capable of detecting forces and moments in three directions or a 6-axis force sensor capable of detecting forces and moments in six directions is used.

While one of the pair of enable switches 81 provided on the opposite sides of the outer peripheral surface 80a of the operation unit 80 is pressed such that movement of the arm 60 is allowed in the aforementioned embodiment, the present disclosure is not limited to this. For example, both of the pair of enable switches 81 provided on the opposite sides of the outer peripheral surface 80a of the operation unit 80 may alternatively be pressed such that movement of the arm 60 is allowed.

While the pair of enable switches 81 are provided on the opposite sides of the outer peripheral surface 80a of the operation unit 80 in the aforementioned embodiment, the present disclosure is not limited to this. For example, one enable switch 81 may alternatively be provided on one side of the outer peripheral surface 80a of the operation unit 80.

While the cross-section of the operation unit 80 has a substantially rectangular shape (the operation unit 80 has a substantially prismatic shape) in the aforementioned embodiment, the present disclosure is not limited to this. For example, the operation unit 80 may alternatively have a substantially cylindrical shape.

While the joystick 82 is provided on the end face 80c that intersects with the outer peripheral surface 80a of the operation unit 80 in the aforementioned embodiment, the present disclosure is not limited to this. In the present disclosure, it is only necessary to provide the joystick 82 at the position operable by the finger of the operator O while the operator O grasps the operation unit 80 to press the enable switches 81.

While the operation unit 80 is supported by the translation mechanism 70 in the aforementioned embodiment, the present disclosure is not limited to this. For example, the operation unit 80 may alternatively be supported by the arm portion 61.

While the joystick 82 operates the arm 60 in the mode for translating the tip end 4d of the medical device 4 in the predetermined plane (see FIG. 7) and the mode for rotating the medical device 4 about the tip end 4d of the medical device 4 (see FIG. 8) in the aforementioned embodiment, the present disclosure is not limited to this. For example, the joystick 82 may alternatively be configured to operate the arm 60 such that the medical device 4 translates along the longitudinal direction of the medical device 4.

While the controller 31 performs both of setting the upper limit for the input signal from the joystick 82 and smoothing the input signal from the joystick 82 in the aforementioned embodiment, the present disclosure is not limited to this. For example, the controller 31 may alternatively perform only one of setting the upper limit for the input signal from the joystick 82 and smoothing the input signal from the joystick 82.

While the four arms 60 are provided in the aforementioned embodiment, the present disclosure is not limited to this. The number of arms 60 may alternatively be three.

While each of the arm portion 61 and the positioner 40 includes a 7-axis articulated robot in the aforementioned embodiment, the present disclosure is not limited to this. For example, each of the arm 60 and the positioner 40 may alternatively include an articulated robot having an axis configuration (six axes or eight axes, for example) other than the 7-axis articulated robot.

What is claimed is:

1. A surgical robot comprising:
    an arm; and
    an operation unit supported by the arm; wherein
    the operation unit includes an enable switch provided on a peripheral surface of the operation unit and configured to allow movement of the arm by being pressed, and a joystick positioned on an end face of the operation unit and configured to control a moving direction of the arm; and the enable switch and the joystick are arranged apart from each other within a range to facilitate operation by fingers of one hand of an operator in the operation unit.

2. The surgical robot according to claim 1, wherein the joystick is configured to operate the moving direction and a moving speed of the arm.

3. The surgical robot according to claim 1, wherein the enable switch is provided on the peripheral surface on an outer peripheral surface of the operation unit, and is configured to allow the movement of the arm when the operator grasps the outer peripheral surface of the operation unit and presses the enable switch.

4. The surgical robot according to claim 3, wherein
the operation unit includes a pair of the enable switches provided on opposite sides of the outer peripheral surface of the operation unit; and
at least one enable switch of the pair of enable switches is configured to allow the movement of the arm when the operator grasps the outer peripheral surface of the operation unit and presses the at least one enable switch of the pair of enable switches.

5. The surgical robot according to claim 4, wherein
the operation unit has a cross-section having a substantially rectangular shape; and
the pair of enable switches are provided on side surfaces of the operation unit that face each other, respectively.

6. The surgical robot according to claim 1, wherein the joystick is arranged at a position on the end face operable by a finger of the operator while the operator grasps an outer peripheral surface of the operation unit and presses the enable switch.

7. The surgical robot according to claim 1, wherein
the arm includes an arm portion including an articulated robot arm, and a translation mechanism provided at a tip end of the arm portion, the translation mechanism being configured to allow a medical device to be attached thereto, the translation mechanism being configured to translate the medical device relative to the arm portion; and
the operation unit is supported by the translation mechanism.

8. The surgical robot according to claim 1, wherein the joystick is configured to operate the arm in one of a translation mode in which the arm moves a medical device attached at a tip end of the arm such that a tip end of the medical device moves on a predetermined plane and a rotation mode in which the arm moves the medical device such that the medical device rotates about the tip end of the medical device.

9. The surgical robot according to claim 1, wherein
the joystick is configured to operate the moving direction and a moving speed of the arm;
the surgical robot further comprises a controller configured to control the arm based on an input signal from the joystick; and
the controller is configured to perform a control to reduce a change in the moving speed of the arm by performing at least one of setting an upper limit for the input signal from the joystick or smoothing the input signal from the joystick.

10. The surgical robot according to claim 1, wherein the operation unit includes a switch unit configured to operate movement of a medical device attached at a tip end of the arm by the arm such that a tip end of the medical device moves along a longitudinal direction of the medical device.

11. A surgical robot comprising:
a robot arm including a plurality of joints, the robot arm being configured to allow a medical device to be attached to a tip end thereof; and
an operation unit supported by the robot arm; wherein
the operation unit includes:
a joystick positioned on an end face of the operation unit and configured to operate the robot arm; and
an enable switch positioned on a peripheral surface of the operation unit and configured to allow movement of the robot arm by being pressed; and
the enable switch and the joystick are arranged apart from each other within a range to facilitate operation by fingers of one hand of an operator in the operation unit.

12. The surgical robot according to claim 11, wherein
the operation unit includes a mode switch configured to switch an operation mode of the joystick; and
the mode switch is configured to be operated to switch between a translation mode in which the robot arm moves the medical device such that a tip end of the medical device moves on a predetermined plane, and a rotation mode in which the robot arm moves the medical device such that the medical device rotates about the tip end of the medical device.

13. The surgical robot according to claim 11, wherein
the operation unit includes a pair of the enable switches provided on opposite sides of an outer peripheral surface of the operation unit; and
at least one of the pair of enable switches is configured to allow the movement of the robot arm by the joystick when the operator grasps the outer peripheral surface of the operation unit and presses the at least one of the pair of enable switches.

14. A surgical robot comprising:
a robot arm including an arm portion including a plurality of joints, and a translation mechanism provided on a tip end of the arm portion, the translation mechanism being configured to allow a medical device to be attached thereto, the translation mechanism being configured to translate the medical device relative to the arm portion; and
an operation unit supported by the robot arm; wherein
the operation unit includes:
a switch unit configured to operate the translation mechanism; and
an enable switch provided on a peripheral surface of the operation unit and configured to allow movement of the robot arm by being pressed; and
the enable switch and the switch unit are arranged apart from each other within a range to facilitate operation by fingers of one hand of an operator of the operation unit.

15. The surgical robot according to claim 14, wherein the operation unit is supported by the translation mechanism so as to be adjacent to the medical device.

16. The surgical robot according to claim 14, wherein the switch unit includes a first switch configured to translate the medical device in a first direction parallel to a longitudinal direction of the medical device, and a second switch configured to translate the medical device in a second direction opposite to the first direction.

17. The surgical robot according to claim 14, wherein the operation unit includes a joystick configured to operate the robot arm.

18. The surgical robot according to claim 17, wherein
the operation unit includes a mode switch configured to switch an operation mode of the joystick; and the mode switch is configured to be operated to switch between a translation mode in which the robot arm moves the medical device such that a tip end of the medical device moves on a predetermined plane, and a rotation mode in which the robot arm moves the medical device such that the medical device rotates about the tip end of the medical device.

19. The surgical robot according to claim 14, wherein the operation unit includes a pair of the switch units provided on opposite sides of an outer peripheral surface of the operation unit; and at least one of the pair of switch units is configured to cause the translation mechanism to translate the medical device when the operator grasps the outer peripheral surface of the operation unit and operates the at least one of the pair of switch units.

\* \* \* \* \*